United States Patent
Filler et al.

(10) Patent No.: US 6,268,517 B1
(45) Date of Patent: Jul. 31, 2001

(54) METHOD FOR PRODUCING SURFACTANT COMPOSITIONS

(75) Inventors: Paul A. Filler, Leander; Elida G. Partain, Cedar Park; Upali Weerasooriya, Austin, all of TX (US)

(73) Assignee: Condea Vista Company, Houston, TX (US)

( * ) Notice: Subject to any disclaimer, the term of this patent is extended or adjusted under 35 U.S.C. 154(b) by 0 days.

(21) Appl. No.: 09/567,670

(22) Filed: May 9, 2000

(51) Int. Cl.$^7$ ................................................ C07C 51/00
(52) U.S. Cl. ................................. 554/156; 534/124
(58) Field of Search ........................ 554/156, 124

(56) References Cited

U.S. PATENT DOCUMENTS

| | | |
|---|---|---|
| 3,663,583 | 5/1972 | Haynes . |
| 5,220,046 | 6/1993 | Leach et al. . |
| 5,386,045 | 1/1995 | Weerasooriya et al. . |
| 6,020,509 | 2/2000 | Weerasooriya et al. . |

Primary Examiner—Deborah D. Carr
(74) Attorney, Agent, or Firm—Browning Bushman

(57) ABSTRACT

A process for producing a surfactant composition by partially saponifying an alkoxylated triglyceride having the formula:

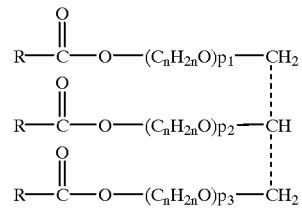

[I]

with an alkali metal hydroxide such as sodium hydroxide and in the presence of from 5 to 10% free water, removing water by heating and recovering a surfactant composition comprising soap and moisturizing agents comprised of alkoxylated monoglycerides and unreacted alkoxylated triglycerides.

9 Claims, No Drawings

METHOD FOR PRODUCING SURFACTANT COMPOSITIONS

CROSS-REFERENCE TO RELATED APPLICATIONS OR PATENTS

This application is related to U.S. Pat. No. 6,020,509, which issued Feb. 1, 2000.

BACKGROUND OF THE INVENTION

1. Field of the Invention

The present invention relates to a process for preparing surfactant compositions and, more particularly, to a method for producing a surfactant composition comprising a soap and alkoxylated mono- and diglycerides as moisturizing agents.

2. Description of the Prior Art

Recently, the cosmetic industry has placed greater emphasis on natural ingredients with proven mildness. In particular, ethoxylated (alkoxylated) mono- and diglycerides are known for their mildness and have been recently demonstrated to be effective moisturizing agents. Not only do these ethoxylated glycerides appear to have excellent moisturizing and mildness characteristics, they also possess surfactant properties; e.g., they are non-ionic surfactants. Accordingly, while theoretically they could be incorporated into a soap composition—.g., a skin cleanser—to impart moisturizing characteristics, it would clearly be desirable to have a process wherein there was produced, in a single reaction, a skin cleanser containing both soap and the ethoxylated glycerides.

It is known that hydroxylated, ethoxylated triglycerides of fatty acids—e.g., ethoxylated castor oil-can be partially saponified to form a polyoxyethylene fatty acid alkali soap. Thus, in U.S. Pat. No. 3,663,583, there is described a process for producing a saponified ethoxylated triglyceride of ricinoleic acid. Ricinoleic acid is a hydroxy fatty acid having the structure:

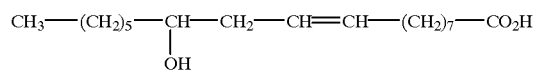

which produces a triglyceride having the following structure:

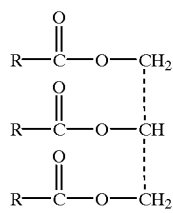

wherein R stands for the fatty portion of the ricinoleic acid—i.e., the portion containing the hydroxyl group and the olefinic linkage. In the process described in U.S. Pat. No. 3,663,583, conventional ethoxylation catalysts such as NaOH and KOH are used to effect the ethoxylation of the hydroxytriglyceride. As would be expected, this results in ethoxylating the hydroxy group of the castor oil such that subsequent saponification cleaves the triglyceride portion of the molecule, resulting in the formation of the polyoxyethylene ricinoleate soap. Thus, the process of U.S. Pat. No. 3,663,583 does not produce a surfactant composition that, in addition to having a soap, also contains mono-and diethoxylated glycerides to act as moisturizing agents.

It is known from U.S. Pat. No. 5,386,045 that alkoxylated triglycerides or triesters having the formula:

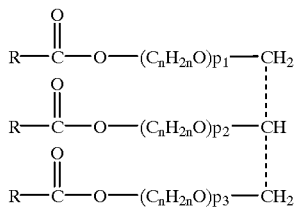

[I]

wherein n is from 2 to 4, $p_1$, $p_2$, and $p_3$ are each from about 1 to about 50, preferably 1 to 15, and R is an organic radical containing from about 6 to about 30 carbon atoms, preferably a linear or branched chain alky group, can be prepared starting by reacting an alkylene oxide, e.g., ethylene oxide, with a triglyceride having the formula:

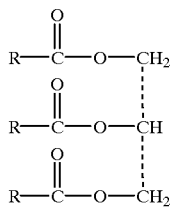

As disclosed in U.S. Pat. No. 5,386,045, the reaction is generally conducted at a temperature of from about 80° C. to about 200° C. and a pressure that can range from subambient up to about 100 psi or higher. A catalytic effective amount of a calcium catalyst is employed in the reaction. The catalyst is selected from the group consisting of (a) Calcium Catalyst A, formed by reacting a reactant mixture comprising an alkoxylated alcohol mixture containing compounds having the general formula:

$$R_1\text{—}O\text{—}(C_nH_{2n}O)_p\text{—}H$$

wherein $R_1$ is an organic radical containing from about 1 to about 30 carbon atoms, preferably a linear or branched chain alkyl group, and p is from 1 to 50, preferably 1 to 15, a calcium-containing compound that is at least partially dispersible in said alkoxylated alcohol, an inorganic acid compound, and a metal alkoxylate of an acidic metal, the calcium-containing compound and the alkoxylated alcohol mixture being mixed prior to addition of the metal alkoxide, the reactant mixture being heated to a temperature and for a time sufficient to effect at least a partial exchange reaction between the alkoxide groups of said metal alkoxide and the hydroxyl groups of the alkoxylated alcohol; (b) Calcium Catalyst B, formed by solubilizing, at least partially, a calcium-containing compound with an activator having the formula:

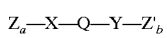

$$Z_a\text{—}X\text{—}Q\text{—}Y\text{—}Z'_b$$

wherein X and Y are the same or different electro-negative, hetero-atoms selected from the group consisting of oxygen, nitrogen, sulfur, and phosphorus, a and b are the same or different integers satisfying the valency requirements of X and Y, Q is an organic radical that is electro-positive or essentially neutral relative to X and/or Y and Z and Z' are the same or different and are either hydrogen or an organic radical that does not prevent said solubilizing; and (c) mixtures of Calcium Catalyst A and Calcium Catalyst B.

In U.S. Pat. No. 6,020,509, there is disclosed a process for producing a surfactant composition containing a conventional soap in admixture with moisturizing agents. In the process disclosed in U.S. Pat. No. 6,020,509, incorporated herein by reference for all purposes, an alkoxylated triglyceride is partially saponified with an alkali metal hydroxide, the process being conducted in the presence of a minimal amount of free water. While the process disclosed in U.S. Pat. No. 6,020,509 produces the desired product, it suffers from the infirmity that the time to saponify the triglyceride is unacceptably long.

SUMMARY OF THE INVENTION

It is therefore an object of the present invention to provide a process for producing a surfactant composition containing a conventional soap in admixture with moisturizing agents.

Another object of the present invention is to provide a process for producing, in a single step reaction, a moisturizing skin cleanser.

The above and other objects of the present invention will become apparent from the description given herein and the appended claims.

According to the process of the present invention, an alkoxylated triglyceride of Formula I is partially saponified with an alkali metal hydroxide, in the presence of from about 5 to about 10% by weight water based on the weight of alkoxylated triglyceride, to produce a surfactant composition containing a soap having the formula:

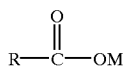

[II]

wherein M is an alkali metal, and a mixture of unreacted alkoxylated triglyceride, alkoxylated monoglyceride and alkoxylated diglyceride, the surfactant composition being recovered. A primary feature of the invention is that by conducting the saponification in the presence of free water, the time to saponify the triglyceride is drastically reduced.

DESCRIPTION OF THE PREFERRED EMBODIMENT

As noted above, the alkoxylated triglycerides, which are used as starting materials in the process of the present invention, are obtained from the alkoxylation of suitable triglycerides, as more fully disclosed in U.S. Pat. No. 5,386,045. Non-limiting examples of the triglycerides that can be used to form the alkoxylated triglycerides used as the starting material in the process of the present invention include triglycerides such as tributyrin, trilaurin, tristearin, etc. In general, any triglyceride of a fatty acid that does not contain a hydroxyl group in the fatty acid chain can be employed as a triglyceride starting material to form the alkoxylated triglycerides of the present invention. The triglycerides that are used to form the alkoxylated triglyceride starting materials of the present invention can be readily derived from natural sources such as whale oil, beeswax, carnauba wax, animal fat, and vegetable sources, such as palm oil, palm kernel oil, coconut oil, olive oil, cottonseed oil, soybean oil, peanut oil, etc.

The alkoxylated triglycerides of the present invention, which as noted above can be produced according to the process described above and in greater detail in U.S. Pat. No. 5,386,045, will have the general formula:

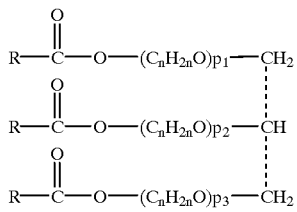

[I]

wherein n is from 2 to 4, $p_1$, $p_2$, and $p_3$ are each from about 1 to about 50, preferably 4 to 20, and R is an organic radical containing from about 6 to about 30 carbon atoms, and provided that the R group contains no hydroxyl groups. It is understood that the R group can contain ether linkages, ketonic structures, etc., the proviso being that the R group contain no active hydrogen atoms or other groupings that would react with the alkali metal hydroxides. Preferably, R will be a branched or straight-chain hydrocarbon radical— i.e., an alkyl group, straight-chain or linear hydrocarbon radicals being particularly preferred. An especially desirable group of alkoxylated triglycerides are those wherein R is a branched or straight-chain hydrocarbon radical—i.e., an alkyl group having from about 6 to about 30 carbon atoms, especially from about 6 to about 20 carbon atoms.

The alkali metal hydroxide used to saponify the alkoxylated triglyceride can be sodium hydroxide, potassium hydroxide, lithium hydroxide, etc., sodium hydroxide being preferred because of its ready availability and low cost. In general, the molar ratio of alkoxylated triglyceride to alkali metal hydroxide will be greater than 0.5 and less than 3, preferably from 1:1 to 1:2.5, most preferably from 1:1 to 1:2.

As noted above, the alkoxylated triglyceride is only partially saponified with the alkali metal hydroxide; i.e., there is insufficient alkali metal hydroxide relative to the amount of alkoxylated triglyceride to cleave all of the carboxyl linkages, which would result in a high make of alkoxylated glycerol. Indeed, it is a feature of the process of the present invention that the surfactant composition produced has relatively low levels of alkoxylated glycerol and that, by varying the amount of alkali metal hydroxide relative to the amount of alkoxylated triglyceride, the surfactant composition can be tailored such that the balance between the soap portion of the composition and the mixture of ethoxylated mono- and diglycerides can be controlled; i.e., the surfactant composition can be tailored to have a higher or lower amount of the soap component and concomitantly a lower or higher amount of the moisturizing agents.

The reaction between the alkoxylated triglyceride and the alkali metal hydroxide can be conducted at temperatures ranging from 25° C. to 175° C. and over a wide pressure range—e.g., from subatmospheric to 50 psi.

In the process disclosed in U.S. Pat. No. 6,020,509, the amount of water present during the saponification was kept to a minimum. Indeed, other than a relatively small amount of water—i.e., approximately 4% by weight—that was present in the base, e.g., sodium hydroxide solution, only a very slight amount of water was added to prevent the reaction mixture from forming alkoxides. As was noted in U.S. Pat. No. 6,020,509, the addition of small amounts of water destroys the alkoxide and converts it back to the base.

It has now been discovered that if, in addition to the water present in the base, from about 5 to about 10% by weight free water based on the weight of the triglyceride is added in the saponification step, the time to obtain the desired degree of saponification can be drastically reduced. For example, an ethoxylated tallow triglyceride containing 80% by weight ethylene oxide saponified to 2 equivalents of saponification takes as long as two working days, while smaller molecules such as laurel triglyceride ethoxylates containing 50% by weight ethylene oxide, could be saponified to 1.2 equivalents in as little as 4 hours. This difference in time reflects the extent of saponification desired and the relative size of the molecules. By using the process of the present invention, saponification is independent of molecule size. Thus, the process of the present invention differs from the process disclosed in U.S. Pat. No. 6,020,509 in the fact that after the base, e.g., sodium hydroxide, is added, an amount of water, e.g., from 5 to 10% based on the weight of the ethoxylated triglyceride, is added to the mixture with stirring. The reaction mixture containing the additional water is then increased to a temperature sufficient to drive off excess water, generally a temperature of from 110° C. to 170° C., the reaction mixture containing the water being maintained at the desired temperature until excess water has been driven off.

To more fully illustrate the invention, the following non-limiting examples are presented:

EXAMPLE 1

About 500 g of 60% Tricoco ETO (ethoxylated coconut oil containing 70% by weight ethoxylated oxide) was melted in a 3-neck round bottom flask equipped with a nitrogen inlet and an overhead stirrer and heated to 140° C. using an oil bath. Sodium hydroxide was added in slowly as a 50% solution. The amount of NaOH used was based on the desired degree of saponification. A slow nitrogen flow was maintained in the flask in order to m minimize discoloration due to the adventitious presence of air. The extent of saponification was monitored until the desired level (1.6 equivalents) was reached. It was found that the time to reach this degree of saponification was approximately 8 hours.

EXAMPLE 2

About 500 g of ethoxylated triglyceride of Example 1 was melted in a 3-neck round bottom flask equipped with a nitrogen inlet and an overhead stirrer and heated to 95° C. using a heating mantel. Sodium hydroxide was added as a 50% solution with stirring. The amount of NaOH used was based on the desired degree of saponification. After the base was added, an additional 3% by weight water based on the weight of triglyceride was added to the mixture with stirring. A slow nitrogen flow was maintained in the flask in order to minimize discolorization due to the adventitious presence of air. After 15–30 minutes, the temperature was increased to 160° C. to improve mixing and to drive off excess water. As soon as the temperature approached 160° C., a sample was taken and titrated to determine the extent of saponification. The sample was maintained at 160° C. for at least 0.5 hour to drive off water. It was found that after 1 hour and 26 minutes, the degree of saponification was 0.929 equivalents.

EXAMPLE 3

The procedure of Example 2 was followed, with the exception that additional 7% by weight water was added. After a reaction time of 30 minutes, the degree of saponification was found to be 1.6 equivalents.

EXAMPLE 4

The procedure of Example 2 was followed, with the exception that an additional 20% by weight water was added. After 19 minutes, the reaction was terminated due to excessive foaming. The degree of saponification was 1.324 equivalents.

EXAMPLE 5

The procedure of Example 2 was followed, with the exception that 60% Tritallow ETO (ethoxylated tallow oil containing 60% by weight ethoxylated oxide) was employed. After 30 minutes of reaction, the degree of saponification was found to be 1.6 equivalents.

EXAMPLE 6

The procedure of Example 1 was followed, with the exception that the triglyceride of Example 5 was employed. It took approximately 12 hours to obtain 1.6 equivalents of saponification.

As can be seen from the above examples, the process of the present invention dramatically reduces the amount of time required to achieve the desired degree of saponification. Note, for example, that in comparing Examples 1 and 3, to achieve 1.6 equivalents of saponification using the prior art process disclosed in U.S. Pat. No. 6,020,509, it takes approximately 8 hours, whereas using the process of the present invention, the same degree of saponification can be achieved in 30 minutes. Likewise, by comparing Examples 5 and 6, it can be seen that by using the prior art process of U.S. Pat. No. 6,020,509, it takes approximately 12 hours to achieve 1.6 equivalents of saponification, whereas using the process of the present invention, the same degree of saponification can be achieved in 30 minutes.

It can also be seen from the examples above that if too little water is present (see Example 2), although the time to achieve saponification is reduced, it is still much longer than can be achieved using the process of the present invention wherein an amount of water of from 5 to 10% by weight is employed. Likewise, and as seen by Example 4, excessive amounts of water lead to foaming, albeit that saponification times are reduced.

It can thus be seen that by using from 5 to 10% by weight water in excess of that present in the base solution used for the saponification, one can markedly decrease the amount of time required to achieve a desired degree of saponification without concomitant foaming, which would render the reaction impractical on a commercial scale.

Quite unexpectedly, it was found that by using the process of the present invention, there was no increase in the amount of polyethoxylated glycerol (PEG) produced. Indeed, it was found that using the process of the present invention, the amount of PEG produced was no greater than that produced by the prior art method disclosed in U.S. Pat. No. 6,020,509.

The foregoing description and examples illustrate selected embodiments of the present invention. In light thereof, variations and modifications will be suggested to one skilled in the art, all of which are in the spirit and purview of this invention.

What is claimed is:

1. A process for producing a surfactant composition comprising reacting an alkoxylated triglyceride having the formula:

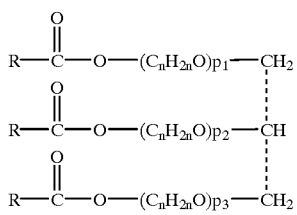

wherein n is from 2 to 4, $p_1$, $p_2$, and $p_3$ are each from about 1 to about 50, and R is an organic radical containing from about 1 to about 30 carbon atoms, with an alkali metal hydroxide to form a reaction mixture pre-mix, the mol ratio of alkoxylated triglyceride to alkali metal hydroxide being from 1:1 to 1:2.5, adding to said reaction mixture pre-mix from about 5 to about 10% by weight free water based on the weight of said alkoxylated triglyceride to form a reaction mixture, maintaining said reaction mixture at a temperature sufficient to remove water, and recovering a surfactant composition comprising a soap having the general formula:

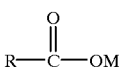

wherein M is an alkali metal, and a mixture of unreacted alkoxylated triglyceride, alkoxylated diglyceride, and alkoxylated monoglyceride.

2. The process of claim 1 wherein the mol ratio of alkoxylated triglyceride to alkali metal hydroxide is 1:1 to 1:2.

3. The process of claim 1 wherein the alkali metal hydroxide is sodium hydroxide.

4. The process of claim 1 wherein n is 2.

5. The process of claim 1 wherein R contains from 6 to 30 carbon atoms.

6. The process of claim 5 wherein R is a linear or branched-chain, saturated or unsaturated alkyl group.

7. The process of claim 1 wherein $p_1$, $p_2$, and $p_3$ are each from about 4 to about 20.

8. The process of claim 1 wherein the alkoxylated triglyceride is formed from a triglyceride derived from a natural source.

9. The process of claim 1 wherein R is a linear or branched chain alkyl group.

* * * * *